United States Patent [19]

Boschelli et al.

[11] Patent Number: 5,356,926

[45] Date of Patent: Oct. 18, 1994

[54] 3-ALKYLOXY-, ARYLOXY-, OR ARYLALKYLOXY-BENZO [β]THIOPHENE-2-CARBOXAMIDES AS INHIBITORS OF CELL ADHESION

[75] Inventors: Diane H. Boschelli, Plymouth; David T. Connor; Clifford D. Wright, both of Ann Arbor, all of Mich.

[73] Assignee: Warner-Lambert Company, Morris Plains, N.J.

[21] Appl. No.: 15,005

[22] Filed: Feb. 9, 1993

Related U.S. Application Data

[63] Continuation-in-part of Ser. No. 840,361, Feb. 24, 1992, Pat. No. 5,208,253.

[51] Int. Cl.$^5$ .................... A61K 31/38; C07D 333/68
[52] U.S. Cl. .................... 514/445; 549/52; 549/53; 549/54; 549/55
[58] Field of Search ............... 549/52, 53, 54, 55; 514/445

[56] References Cited

U.S. PATENT DOCUMENTS 4,703,053 10/1987 Connor et al. .................. 514/382
4,800,211 1/1989 Tischler et al. .................. 514/443

OTHER PUBLICATIONS

*Nature*, vol. 346, pp. 425–434 (1990).
*Thrombosis and Haemostasis*, vol. 65 (3), 223–228 (1991).
*Clinical and Experimental Allergy*, vol. 20, 619–626 (1990).
*Transplantation*, vol. 48, No. 5, 727–731 (1989).
*Biochemical Pharmacology*, vol. 40, No. 8, 1683–1687 (1990).
*Proc. Natl. Acad. Sci.*, vol. 84, 9238–9242 (1987).
*J. Clin. Invest.*, vol. 82, 1746–1756 (1988).
*The Journal of Immunology*, vol. 137, No. 6, 1893–1896 (1986).
*Blood*, vol. 78, No. 10, 2721–2726 (1991).

*Primary Examiner*—Richard L. Raymond
*Attorney, Agent, or Firm*—Ronald A. Daignault; Charles W. Ashbrook

[57] ABSTRACT

3-Alkyloxy-, aryloxy-, or arylalkyloxybenzo[b]-thiophene-2-carboxamides are described as agents which block leukocyte adherence to vascular endothelium and, as such, are effective therapeutic agents for treating inflammatory diseases. Certain of these compounds are novel and methods of preparation are also described.

11 Claims, No Drawings

3-ALKYLOXY-, ARYLOXY-, OR ARYLALKYLOXY-BENZO [β]THIOPHENE-2-CARBOXAMIDES AS INHIBITORS OF CELL ADHESION

This is a continuation-in-part of U.S. application Ser. No. 840,361 filed Feb. 24, 1992, now U.S. Pat. No. 5,208,253.

BACKGROUND OF THE INVENTION

The present invention is for the use of certain 3-alkyloxy-, aryloxy-, or arylalkyloxybenzo[b]-thiophene-2-carboxamides, and pharmaceutically acceptable salts thereof, to prevent the adhesion of leukocytes to endothelial cells. Leukocyte adherence to vascular endothelium is integral to the pathogenesis of inflammation. The adhesion process precedes transendothelial migration of leukocytes into surrounding tissue and ensuing tissue damage. Compounds that can block this initial adhesive interaction are expected to have efficacy in the treatment of inflammatory diseases such as rheumatoid arthritis, asthma, and psoriasis. Other indications would include but are not limited to adult respiratory distress syndrome, reperfusion injury, ischemia, ulcerative colitis, vasculitides, atherosclerosis, inflammatory bowel disease, and tumor metastases.

Adhesion receptors are organized into three main families: the selectins, the immunoglobulin superfamily, and the integrins (*Nature* 1990;346:426). Members of all three classes are involved in mediating leukocyte adhesion during inflammation (for reviews of this area see: *Thrombosis and Hemostasis* 1991;65(3):223), *Clinical and Experimental Allergy* 1990;20:619, *Transplantation* 1989;48:727, *Biochemical Pharm.* 1990;40(8):1683). Endothelial leukocyte adhesion molecule-1 (ELAM-1 or E-selectin) is a member of the selectin family of glycoproteins that promote cell-cell adhesion. ELAM-1 is reported to be maximally expressed on the surface of endothelial cells 4 hours after stimulation of the endothelial cells with cytokines, such as interleukin-1 (IL-1) or tumor necrosis factor α (TNF-α) or other inflammatory mediators, such as lipopolysaccharide (LPS) (*Pro. Nat. Acad. Sci.* 1987;84:9238).

Intercellular adhesion molecule-1 (ICAM-1) is a member of the immunoglobulin superfamily. It is also upregulated with maximum expression occurring 12 to 24 hours after stimulus. It has been shown that 4 hours after the endothelial cells are stimulated with an inflammatory mediator, both ELAM-1 and ICAM-1 are present on the cell surface (*J. Clin. Invest.* 1988;82:1746 and *J. Immun,* 1986;137:1893, *Blood* 1991;78:2721).

The 3-alkyloxy-, aryloxy-, and arylalkyloxybenzo[b]-thiophene-2-carboxamides of the present invention have been shown in an in vitro assay to prevent the adhesion of neutrophils to human umbilical vein endothelial cells (HUVECS) stimulated with TNFα.

The 3-alkyloxy-, aryloxy-, and arylalkyloxybenzo[b]-thiophene-2-carboxamides of the present invention are new but are included in the generic scope of U.S. Pat. No. 4,800,211 as possible dual inhibitors of cyclooxygenase and 5-lipoxygenase. The specific compounds of the present invention do not significantly inhibit isolated 5-lipoxygenase.

SUMMARY OF THE INVENTION

Accordingly, the present invention is for the use of a compound of the formula (I) and pharmaceutically acceptable salts thereof to inhibit the adhesion of leukocytes to stimulated human endothelial cells, thereby providing for the treatment of inflammatory diseases:

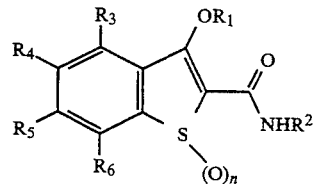

wherein $R_1$ is lower alkyl, phenyl, or benzyl;

$R_2$ is hydrogen, lower alkyl, phenyl, benzyl, thiophene, $(CH_2)_mQ$, or phenyl, benzyl, or thiophene substituted with $(CH_2)_mQ$;

n is an integer from 0 to 2;

m is an integer from 0 to 6;

Q is $CO_2R_7$ where $R_7$ is hydrogen or lower alkyl; and $R_3$, $R_4$, $R_5$, $R_6$ are independently hydrogen, hydroxy, nitro, amino, lower alkyl, and lower alkoxy.

Particularly, the present invention is the use of the following compounds in their free form or as pharmaceutically acceptable salts to treat inflammatory diseases by administering an effective amount in unit dosage form of:

5-methoxy-3-(1-methylethoxy)benzo[b]thiophene-2-carboxamide;

3-(1-methylethoxy)benzo[b]thiophene-2-carboxamide;

5-chloro-3-(1-methylethoxy)benzo[b]thiophene-2-carboxamide;

5-methyl-3-(1-methylethoxy) benzo[b]thiophene-2-carboxamide;

3-(1-methylethoxy)-5-nitrobenzo[b]thiophene-2-carboxamide;

7-methoxy-3-(1-methylethoxy)benzo[b]thiophene-2-carboxamide;

3,5-dimethoxybenzo[b]thiophene-2-carboxamide;

5-methoxy-3-(phenylmethoxy)benzo[b]thiophene-2-carboxamide;

5-methoxy-3-(phenoxy)benzo[b]thiophene-2-carboxamide;

5-hydroxy-3-(1-methylethoxy)benzo[b]thiophene-2-carboxamide;

6-methoxy-3-(1-methylethoxy) benzo[b]thiophene-2-carboxamide;

4-[[[5-methoxy-3-(1-methylethoxy)benzo[b]thien-2-yl]carbonyl]amino]-benzoic acid;

3-[[[5-methoxy-3-(1-methylethoxy) benzo[b]thien-2-yl]carbonyl]amino]benzoic acid;

ethyl 2-[[[5-methoxy-3-(1-methylethoxy)benzo[b]thien-2-yl]carbonyl]arnino]benzeneacetate 2-[[[5-methoxy-3-(1-methylethoxy)benzo[b]thienyl]-carbonyl]amino]benzoic acid;

4-[[[5-methoxy-3-(1-methylethoxy)benzo[b]thienyl]-carbonyl]aminomethyl]benzoic acid;

methyl 4-[[[5-methoxy-3-(1-methylethoxy)benzo[b]-thien-2-yl]carbonyl]amino]benzeneacetate;

4-[[[5-methoxy-3-(1-methylethoxy)benzo[b]thienyl]-carbonyl]arnino]benzeneacetic acid;

methyl 3-[[[5-methoxy -3-(1-methylethoxy)benzo[b]-thien-2-yl ]carbonyl ]amino]benzeneacetate;

3-[[[5-methoxy-3-(1-methylethoxy)benzo[b]thien-2-yl]carbonyl]amino]benzeneacetic acid;

methyl 5-[[[5-methoxy-3-(1-methylethoxy)benzo[b]-thien-2-yl]carbonyl]amino]pentanoate;

5-[[[5-methoxy-3-(1-methylethoxy)benzo[b]thien-2-yl]carbonyl]amino]pentanoic acid;

3-[[[5-methoxy-3-(1-methylethoxy)benzo[b]thien-2-yl]carbonyl]amino-2-thiophenecarboxylic acid;

5-methoxy-N-methyl-(3-(1-methylethoxy)benzo[b]-thiophene-2-carboxamide;

N-ethyl-(5-methoxy-3-(1-methylethoxy)benzo[b]thiophene-2-carboxamide;

5-methoxy-3-(1-methylethoxy)-N-phenylbenzo[b]thiophene-2-carboxamide;

5-methoxy-3-(1-methylethoxy)-N-(phenylmethyl)-benzo[b]thiophene-2-carboxamide;

5-methoxy-3-(1-methylethoxy)benzo[b]thiophene-2-carboxamide-1-oxide;

5-methoxy-3-(1-methylethoxy)benzo[b]thiophene-2-carboxamide-1,1'-dioxide;

3-(1,1-dimethylethoxy)-5-methoxybenzo[b]thiophene-2-carboxamide;

6-chloro -3-(1-methylethoxy)benzo[b]thiophene-2-carboxamide;

5-amino-3-(1-methylethoxy)benzo[b]thiophene-2-carboxamide;

methyl 4-[[[5-methoxy-3-(1-methylethoxy)benzo[b]-thien-2-yl]carbonyl]amino]butanoate;

4-[[[5-methoxy-3-(1-methylethoxy)benzo[b]thien-2-yl]carbonyl]amino]butanoic acid;

5-methoxy-3-(1-methylethoxy)-N-(1-methylethyl)-benzo[b]thiophene-2-carboxamide;

ethyl 6-[[[5-methoxy-3-(1-methylethoxy)benzo[b]thien-2-yl]carbonyl]amino]-3-pyridinecarboxylate;

6-[[[5-methoxy-3-(1-methylethoxy)benzo[b]thien-2-yl]carbonyl]amino]-3-pyridinecarboxylic acid;

ethyl 2-[[[5-methoxy-3-(1-methylethoxy)benzo[b]thien-2-yl]carbonyl]amino]-4-thiazoleacetate;

2-[[[5-methoxy-3-(1-methylethoxy)benzo[b]thien-2-yl]carbonyl]amino]-4-thiazoleacetic acid;

3-methoxy-4-[[[5-methoxy-3-(1-methylethoxy)benzob]thien-2-yl]carbonyl]amino]benzoic acid;

methyl 2-hydroxy-4-[[[5-methoxy-3-(1-methylethoxy)benzo[b]thien-2-yl]carbonyl]amino]benzoate;

2-hydroxy -4-[[[5-methoxy -3-(1-methylethoxy)benzo[b]thien-2-yl]carbonyl]amino]benzoic acid;

methyl 4-[[[5-methoxy-3-(1-methylethoxy) benzo[b]-thien-2-yl]carbonyl]amino]benzenesulfonate;

N-[1-(hydroxymethyl)-1-methylethyl]-5-methoxy-3-(1-methylethoxy)benzo[b]thiophene-2-carboxamide;

N-ethyl-5-methoxy-3-(1-methylethoxy)benzo[b]thiophene-2-carboxamide-1-oxide;

5-methoxy-N-methyl-3-(1-methylethoxy)benzo[b]thiophene-2-carboxamide-1-oxide;

5-methoxy-3-(1-methylethoxy)-N-(phenylmethyl)-benzo[b]thiophene-2-carboxamide-1-oxide;

methyl 3-[[[5-methoxy-3-(1-methylethoxy)benzo[b]-thien-2-yl]carbonyl]amino]benzeneacetate-1-oxide;

5-hydroxy-3-(1-methylethoxy)benzo[b]thiophene-2-carboxamide-1-oxide;

5-methyl-3-(1-methylethoxy)benzo[b]thiophene-2-carboxamide -1-oxide;

5-methoxy-3-phenoxybenzo[b]thiophene-2-carboxamide-1-oxide;

5-methoxy-3-(1-methylethoxy)-N-(1-methylethoxy)-benzo[b]thiophene-2-carboxamide-1-oxide; or 3,5-dimethoxybenzo[b]thiophene-2-carboxamide-1-oxide.

The present invention also includes the following novel compounds or their pharmaceutically acceptable acid addition salts thereof:

5-chloro-3-(1-methylethoxy)benzo[b]thiophene-2-carboxamide;

5-methyl -3-(1-methylethoxy)benzo[b]thiophene-2-carboxamide;

3-(1-methylethoxy)-5-nitrobenzo[b]thiophene-2-carboxamide;

7-methoxy-3-(1-methylethoxy)benzo[b]thiophene-2-carboxamide;

3,5-dimethoxybenzo[b]thiophene-2-carboxamide;

5-methoxy-3-(phenylmethoxy)benzo[b]thiophene-2-carboxamide;

5-methoxy-3-(phenoxy)benzo[b]thiophene -2-carboxamide;

5-hydroxy-3-(1-methylethoxy)benzo[b]thiophene-2-carboxamide;

6-methoxy-3-(1-methylethoxy)benzo[b]thiophene-2-carboxamide;

ethyl 2-[[[5-methoxy-3-(1-methylethoxy)benzo[b]thien-2-yl]carbonyl]amino]benzeneacetate;

4-[[[5-methoxy-3-(1-methylethoxy)benzo[b]thien-2-yl]carbonyl]aminomethyl ]benzoic acid;

methyl 4-[[[5-methoxy-3-(1-methylethoxy)benzo[b]-thien-2-yl]carbonyl]amino]benzeneacetate;

4-[[[5-methoxy-3-(1-methylethoxy)benzo[b]thienyl]-carbonyl]arnino]benzeneacetic acid;

methyl 3-[[[5-methoxy-3-(1-methylethoxy)benzo[b]-thien-2-yl]carbonyl]amino]benzeneacetate;

3-[[[5-methoxy-3-(1-methylethoxy)benzo[b]thienyl]-carbonyl]amino]benzeneacetic acid;

methyl 5-[[[5-methoxy-3-(1-methylethoxy)benzo[b]-thien-2-yl]carbonyl]amino]pentanoate;

5-[[[5-methoxy-3-(1-methylethoxy)benzo[b]thienyl]-carbonyl]amino]pentanoic acid;

5-methoxy-N-methyl-(3-(1-methylethoxy)benzo[b]-thiophene-2-carboxamide;

N-ethyl-(5-methoxy-3-(1-methylethoxy)benzo[b]thiophene-2-carboxamide;

5-methoxy-3-(1-methylethoxy)-N-phenylbenzo[b]thiophene-2-carboxamide;

5-methoxy-3-(1-methylethoxy)-N-(phenylmethyl)-benzo[b]thiophene-2-carboxamide;

5-methoxy-3-(1-methylethoxy)benzo[b]thiophene-2-carboxamide -1-oxide;

5-methoxy-3-(1-methylethoxy)benzo[b]thiophene-2-carboxamide 1,1'-dioxide;

3-(1,1-dimethylethoxy)-5-methoxybenzo[b]thiophene-2-carboxamide;

6-chloro-3-(1-methylethoxy)benzo[b]thiophene-2-carboxamide;

5-amino-3-(1-methylethoxy)benzo[b]thiophene-2-carboxamide;

methyl 4-[[[5-methoxy-3-(1-methylethoxy)benzo[b]-thien-2-yl]carbonyl]amino]butanoate;

4-[[[5-methoxy-3-(1-methylethoxy)benzo[b]thienyl]-carbonyl]amino]butanoic acid;

5-methoxy-3-(1-methylethoxy)-N-(1-methylethyl)-benzo[b]thiophene-2-carboxamide;

ethyl 6-[[[5-methoxy-3-(1-methylethoxy)benzo[b]thien-2-yl]carbonyl]amino]-3-pyridinecarboxylate; 6-[[[5-methoxy-3-(1-methylethoxy)benzo[b]thienl]carbonyl]amino]-3-pyridinecarboxylic acid;

ethyl 2-[[[5-methoxy-3-(1-methylethoxy)benzo[b]thien-2-yl]carbonyl]amino]-4-thiazoleacetate;

2-[[[5-methoxy-3-(1-methylethoxy)benzo[b]thienyl]-carbonyl]amino]-4-thiazoleacetic acid;

3-methoxy-4-[[[5-methoxy-3-(1-methylethoxy)benzob]thien-2-yl]carbonyl]amino]benzoic acid;

methyl 2-hydroxy-4-[[[5-methoxy-3-(1-methylethoxy)benzo[b]thien-2-yl]carbonyl]amino]benzoate;

2-hydroxy-4-[[[5-methoxy-3-(1-methylethoxy)benzob]thien-2-yl]carbonyl]amino]benzoic acid;

methyl 4-[[[5-methoxy-3-(1-methylethoxy)benzo[b]thien-2-yl]carbonyl]amino]benzenesulfonate;

N-[1-(hydroxymethyl)-1-methylethyl]-5-methoxy-3-(1-methylethoxy)benzo[b]thiophene-2-carboxamide;

N-ethyl-5-methoxy-3-(1-methylethoxy)benzo[b]thiophene-2-carboxamide-1-oxide;

5-methoxy-N-methyl-3-(1-methylethoxy)benzo[b]thiophene-2-carboxamide-1-oxide;

5-methoxy-3-(1-methylethoxy)-N-(phenylmethyl)-benzo[b]thiophene -2-carboxamide -1-oxide;

methyl 3-[[[5-methoxy-3-(1-methylethoxy)benzo[b]thien-2-yl]carbonyl]amino]benzeneacetate -1-oxide;

5-hydroxy-3-(1-methylethoxy)benzo[b]thiophene-carboxamide-1-oxide;

5-methyl-3-(1-methylethoxy)benzo[b]thiophene-2-carboxamide-1-oxide;

5-methoxy-3-phenoxybenzo[b]2-carboxamide-1-oxide;

5-methoxy-3-(1-methylethoxy)-N-(1-methylethoxy)-benzo[b]thiophene-2-carboxamide-1-oxide; or 3,5-dimethoxybenzo[b]thiophene-2-carboxamide-1-oxide.

DETAILED DESCRIPTION

The terms used in defining the compounds of Formula I and the more particular compounds of the present invention are defined as follows:

Lower alkyl and lower alkoxy mean a straight or branched alkyl or alkoxy group having one to four carbon atoms and includes, for example, methyl, ethyl, propyl, i-propyl, or otherwise referred to as (methyl)ethyl, and t-butyl or otherwise referred to as 1,1-(dimethyl)ethyl, and correspondingly, for example, methoxy, ethoxy, i-propoxy or otherwise referred to as 1-(methyl)ethoxy and the like.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge, S. M., et al, "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with inorganic or organic bases, such as metal bases or amines, such as alkali and alkaline earth metal bases, e.g., hydroxides or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al, "Pharmaceutical Salts," *Journal of Pharmaceutical Science* 1977;66:1–19).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solrated forms, including hydrated forms. In general, the solrated forms, including hydrated forms, are equivalent to unsolvated forms and are intended to be encompassed within the scope of the present invention.

In determining when a cell adhesion inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formula I or pharmacologically acceptable salt thereof to achieve a therapeutic effect will, of course, vary both with the particular compound, the route of administration, the mammal under treatment, and the particular disorder of disease concerned. A suitable dose of a compound of Formula I or pharmacologically acceptable salt thereof for a mammal suffering from, or likely to suffer from any condition as described hereinbefore is 0.1 µg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 µg to 100 µg of the compound per kilogram, typically about 0.1 µg/kg.

In the case of oral dosing for the treatment or prophylaxis of arthritis or inflammation in general, due to any course, a suitable dose of a compound of Formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of leukocyte adherence to vascular endothelium, the 5-lipoxygenase enzyme, cyclooxygenase, and thus in treating inflammatory-related diseases or conditions may be demonstrated by their effectiveness in various standard test procedures. A description of each procedure and exemplary test results follows.

METHOD FOR DETERMINING THE INHIBITION OF HUMAN NEUTROPHIL ADHESION TO TNFα, IL-1α, AND LPS-STIMULATED HUMAN UMBILICAL VEIN ENDOTHELIAL CELLS BY 3-ALKYLOXY-, ARYLOXY-, OR ARYLALKYLOXY BENZO[b]THIOPHENE-2-CARBOXAMIDES

Isolation of Neutrophils

Neutrophils were isolated from anticoagulant-treated venous blood obtained from healthy human volunteers according to the method of Ferrante and Thong (*J. Immunol. Methods* 1978;24:389–93). The cell preparations consisted of greater than 98% neutrophils.

Endothelial Cell Culture

Second passage human umbilical vein endothelial cells (HUVEC) (Clonetics, San Diego, Calif.) were seeded into Falcon 24-well cell culture plates (Becton Dickinson, Lincoln Park, N.J.) at approximately $2 \times 10^4$ cells per well. The cells were grown to confluent monolayers in endothelial basal medium (EBM, Clonetics) supplemented with 5% fetal calf serum (Hyclone Laboratories, Logan, Utah), 10 ng/mL EGF, 1 μg/mL hydrocortisone, 0.4% bovine brain extract (Clonetics) in 5% $CO_2$ at 37° C.

Neutrophil Adhesion

Neutrophils ($30 \times 10^6$) were labeled for 60 minutes at 37° C. with 100 μCi $Na^{51}CrO_4$ (ICN Biomedicals, Costa Mesa, Calif.) in 2.0 mL $Ca^{2+}$- and $Mg^{2+}$-free Hanks' balanced salt solution (HBSS, GIBCO Laboratories, Grand Island, N.Y.). The cells were washed two times in HBSS and suspended in unsupplemented EBM.

Stimulation of HUVEC with tumor necrosis factor-α (TNFα) (Genzyme, Cambridge, Mass.), interleukin (IL-1α) (Genzyme) or *E. coli* 0111:B4 lipopolysaccharide (LPS) (Sigma) in the presence or absence of drug was initiated 4 hours prior to the addition of neutrophils. The suspension medium was unsupplemented EBM or supplemented EBM for studies with cytokines or LPS, respectively. Such treatment has been shown to promote maximal expression of the endothelial cell leukocyte adhesion molecule ELAM-1 as well as expression of ICAM-1 (*J. Immunol*, 1986;137:1893); *Proc. Natl. Acad. Sci. USA* 1987:9238). Immediately prior to addition of $^{51}Cr$-labeled neutrophils to the HUVEC monolayers, the cultures were washed with 1 mL unsupplemented media to remove stimulus and/or drug. Neutrophils ($5 \times 10^5$) were then added to the HUVEC in 0.5 mL unsupplemented media and incubated at 37° C. for 30 minutes. Nonadherent neutrophils were removed by aspiration. Following an additional wash, adherent neutrophils were lysed with 0.5 mL 1N $NH_4OH$ overnight at 37° C. Lysates were collected and the radioactivity in each well was determined by gamma ray spectroscopy.

MODIFIED METHOD FOR DETERMINING THE INHIBITION OF HUMAN NEUTROPHIL ADHESION TO TNFα, IL-1α, AND LPS STIMULATED HUMAN UMBILICAL VEIN ENDOTHELIAL CELLS BY 3-ALKOXY-BENZO[b]THIOPHENE-2-CARBOXAMIDES

The previous assay using $^{51}Cr$ labeled human neutrophils has been modified. The neutrophils are now labeled with the fluorescent dye calcein. The current method allows for quantification of neutrophil adherence by fluorescence spectroscopy.

Cell Culture

Second passage HUVEC (Clonetics Corporation, San Diego, Calif., CC-2617) were seeded into Corning (Corning glass works, Corning, N.Y.) 96-well cell culture plates at approximately $5 \times 10^3$ cells/well and grown to confluency in supplemented endothelial basal medium (EBM, MCDB-131, Clonetics, 10 ng/mL EGF, 1 μg/mL hydrocortisone, 0.4% bovine brain extract, 5% Fetal Bovine Serum). One day prior to running the assay, typically 3 days postseeding, the cultures were refed with 0.2 mL/well supplemented EBM (S-EBM).

Preparation of Test Compounds

Test compounds were prepared as 10 mL stock solutions at a concentration of 1.0 mM. The compounds were initially solubilized in 0.1 mL DMSO followed by the addition of 9.9 mL S-EBM. The drug preparations were then diluted in one step to a concentration of 66.6 μM. Solubilizations and dilutions were performed in polystyrene containers.

Isolation of Human Neutrophils

Human neutrophils were isolated from anticoagulant-treated venous blood obtained from healthy volunteers according to the method of Ferrante and Thong. The cell preparations consisted of greater than 98% neutrophils.

Stimulation of HUVEC

Recombinant human tumor necrosis factor-α (TNF, Genzyme, Boston, Mass., code TNF-H) was prepared at 400 U/mL in S-EBM. Stock TNF was prepared to 20,000 U/mL in Delbecco's phosphate-buffered saline (PBS, Gibco, Grand Island N.Y.) plus 0.1% BSA and stored at −70° C. HI/VEC were washed one time with 0.2 mL warm unsupplemented EBM and then stimulated for 4 hours at 37° C. with 200 U/mL TNF in the presence of 33.3 μM test compound. This was accomplished by adding 0.1 mL of 400 U/mL TNF and 0.1 mL 66.6 μM test compound. These additions were done slowly as to not disrupt the HUVEC monolayer. Each compound was tested in six wells. Unstimulated (vehicle control) and TNF-stimulated without test compound treatments were also run in each plate.

Labeling of Neutrophils

One hour prior to adding the neutrophils to the HI/-VEC, neutrophils ($5 \times 10^6$/mL) were labeled for 30 minutes at 37° C. with 5 μM calcine-AM (Molecular Probes, Eugene, OR) in Hanks' balanced salt solution plus 0.45% BSA. Stock calcein was prepared to 5 mM in anhydrous DMSO and stored desiccated at −20° C. At the end of the incubation the cells were washed two times in cold HBSS and resuspended to a final concentration of $1 \times 10^6$ cells/mL in unsupplemented EBM.

Addition of Neutrophils to HUVEC

At the end of the 4-hour stimulation and immediately prior to the addition of the neutrophils to the HUVEC monolayer, the plates were washed with 0.2 mL warm unsupplemented EBM to remove TNF and drug. Neutrophils ($1 \times 10^5$ cells) were slowly added to each of the treated wells and incubated for 30 minutes at 37° C. At the end of the incubation the plates were washed two times with 0.2 mL warm unsupplemented EBM followed by a final addition of 0.1 mL for plate scanning.

Determination of Relative Fluorescence

The relative fluorescence was determined using a Millipore Cytofluor 2300 system (excitation=480, emission=530, sensitivity=4).

Calculations

The assay was considered valid if the TNF-stimulation of the HUVEC resulted in a 300% increase in neutrophil adherence over adherence to unstimulated HUVEC. Results were expressed as means of percent inhibition of TNF-stimulated adherence, using the following equation.

$$\% \text{ Inhibition} = 100 - \left( \frac{\text{stimulated adherence}_{(drug)} - \text{unstimulated adherence}}{\text{stimulated adherence}_{(control)} - \text{unstimulated adherence}} \right) \times 100$$

Compounds which exhibited inhibitory activity of 50% or greater at 33.3 μM were retested at concentrations of 33.3 μM, 10.0 μM, 3.3 μM, and 1.0 μM to determine IC50 values. Linear regression analysis of the means of the inhibition values were used to determine the IC50.

The results obtained with certain compounds of the present invention are shown in Tables 1–3. The compounds of Examples 36–44 in Table 2 and 45–53 in Table 3 were tested according to the modified method.

TABLE 1

Inhibition of Adhesion by 3-Alkoxy-benzo[b]thiophene-2-primary carboxamides

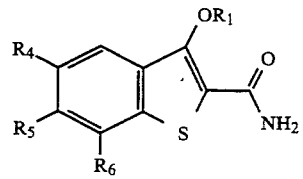

| Example Number | R1 | R4 | R5 | R6 | Adhesion (% Inhibition at 100 μM or IC50, μM) |
|---|---|---|---|---|---|
| 1 | i-Pr | OMe | H | H | 3.8 |
| 2 | i-Pr | H | H | H | (60%) |
| 3 | I—Pr | Cl | H | H | (72%) |
| 4 | i-Pr | Me | H | H | (61%) |
| 5 | i-Pr | NO2 | H | H | (40%) |
| 6 | i-Pr | H | H | OMe | (35%) |
| 7 | Me | OMe | H | H | (60%) |
| 8 | CH2Ph | OMe | H | H | (57%) |
| 9 | Ph | OMe | H | H | (59%) |
| 10 | i-Pr | OH | H | H | 1.2 |
| 11 | i-Pr | H | OMe | H | (24%) |
| 30 | t-Bu | OMe | H | H | (100%) |
| 31 | i-Pr | H | Cl | H | (26%) |
| 32 | i-Pr | NH2 | H | H | (49%) |

TABLE 2

Inhibition of Adhesion by 3-Alkoxy-benzo[b]thiophene-2-substituted carboxamides

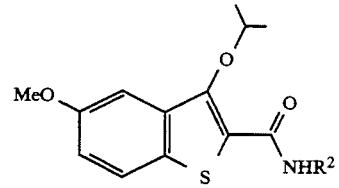

| Example Number | R2 | Adhesion (% Inhibition at 100 μM or IC50, μM) |
|---|---|---|
| 1 | H | 3.8[b] |
| 12 | Ph-p-COOH | 50[b] |

TABLE 2-continued

Inhibition of Adhesion by 3-Alkoxy-benzo[b]thiophene-2-substituted carboxamides

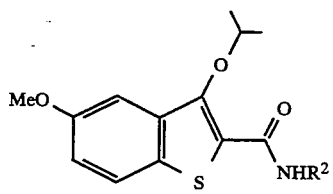

| Example Number | $R^2$ | Adhesion (% Inhibition at 100 μM or $IC_{50}$, μM) |
|---|---|---|
| 13 | Ph-m-COOH | (28%) |
| 14 | Ph-o-COOEt | (32%) |
| 15 | Ph-o-COOH | (35%) |
| 16 | $CH_2$Ph-p-COOH | (47%) |
| 17 | Ph-p-$CH_2$COOMe | (27%) |
| 18 | Ph-p-$CH_2$COOH | (32%) |
| 19 | Ph-m-$CH_2$COOMe | (45%) |
| 20 | Ph-m-$CH_2$COOH | (70%) |
| 21 | $(CH_2)_4$COOMe | (8%) |
| 22 | $(CH_2)_4$COOH | (9%) |
| 23 | thiophene-2-COOH | (20%) |
| 24 | Me | (78%) |
| 25 | Et | (64%) |
| 26 | Ph | (12%) |
| 27 | $CH_2$Ph | (35%) |
| 33 | $(CH_2)_3$COOMe | (100%) |
| 34 | $(CH_2)_3$COOH | (35%) |
| 35 | i-Pr | (100%) |
| 36 | 2-pyridyl-4-$CO_2$Et | $(26\%)^a$ |
| 37 | 2-pyridyl-4-$CO_2$H | $(8\%)^a$ |
| 38 | 2-thiazolyl-4-$CH_2CO_2$Et | $(72\%)^a$ |
| 39 | 2-thiazolyl-4-$CH_2CO_2$H | $(26\%)^a$ |
| 40 | Ph-o-OMe-p-$CO_2$H | $(34\%)^a$ |
| 41 | Ph-m-OH-p-$CO_2$Me | $(32\%)^b$ |
| 42 | Ph-m-OH-p-$CO_2$H | $34^c$ |
| 43 | Ph-p-$SO_2$Me | $(67\%)^b$ |
| 44 | $C(CH_3)_2CH_2OH$ | $(20\%)^b$ |

$^a$Tested at a concentration of 33.3 μM
$^b IC_{50}$ (μM)

TABLE 3

Inhibition of Adhesion by 3-Alkoxy-benzo[b]thiophene-2-carboxamide and Oxides

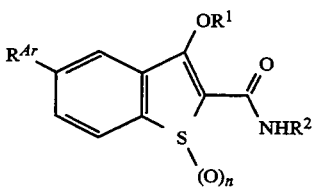

| Example Number | n | $R^1$ | $R^2$ | $R^{Ar}$ | Adhesion (% Inhibition at 100 μM or $IC_{50}$, μM) |
|---|---|---|---|---|---|
| 1 | 0 | i-Pr | H | OMe | 3.8 |
| 28 | 1 | i-Pr | H | OMe | (83%) |
| 29 | 2 | i-Pr | H | OMe | (4%) |
| 45 | 1 | i-Pr | Et | OMe | (36%) |
| 46 | 1 | i-Pr | Me | OMe | (43%) |
| 47 | 1 | i-Pr | Bn | OMe | (15%) |
| 48 | 1 | i-Pr | Ph-p-COOMe | OMe | (6%) |
| 49 | 1 | i-Pr | H | OH | (79%) |
| 50 | 1 | i-Pr | H | Me | (69%) |
| 51 | 1 | Ph | H | OMe | (15%) |
| 52 | 1 | i-Pr | i-Pr | OMe | (8%) |
| 53 | 1 | Me | H | OMe | (40%) |

One of the above compounds, 5-methoxy-3-(1-methylethoxy)benzo[b]thiophene-2-carboxamide, Example 1), gave potent inhibition of the human one-way mixed lymphocyte reaction (MLR). This compound has an $IC_{50}$ of 0.3 μM (n=2). The details of this assay are as follows:

METHOD FOR DETERMINING THE INHIBITION OF THE HUMAN ONE-WAY MIXED LYMPHOCYTE REACTION BY 5-METHOXY3-(1-METHYLETHOXY)BENZO[b]-THIOPHENE-2-CARBOXAMIDE

Lymphocyte Isolation

Heparinized peripheral blood was collected from normal human donors. Lymphocytes were isolated by density gradient centrifugation on Ficoll-Hypaque gradients (10 mL blood to 4 mL Ficoll-Hypaque, specific gravity=1.09 mg/mL, Pharmacia) for 20 minutes at 1200×g at room temperature. Lymphocytes (top layer) were removed and washed three times with Hanks balanced salt solution (HBSS) without magnesium and calcium (MA Bioproducts), centrifuging for 10 minutes at 300 g. Cell viability was determined using trypan blue exclusion. Cells were kept on ice until added to culture plates.

Culture Medium

The final culture medium consisted of RPMI-1640 (Microbiological Associates) supplemented with L-glutamine (2 mM), penicillin (100 IU/mL), streptomycin (100 μg/mL), HEPES buffer (10 mM), and 10% heat-inactivated (56° C., 30 minutes) fetal calf serum (FCS) (Armour).

One-Way Mixed Lymphocyte Reaction (MLR) Cultures

Lymphocytes which were used as stimulators were treated with mitomycin C (50 μg/mL/107 cells) for 20 minutes at 37° C. Cells were washed twice with HBSS not containing magnesium and calcium. Responder cells (50 μL at 8×10$^6$ cells/mL in 40% FCS) were added to 96-well microtiter plate wells with an equal volume and number of allogeneic, mitomycin C-treated stimulator cells (not in FCS). Test materials and media were added in 50-μL aliquots each, such that the final culture conditions were 2×10$^6$ responding cells/mL (4×10$^5$ responding cells/well) in medium containing 10% FCS. Unstimulated responder cells were run as background controls in medium alone and with compound dilutions. Cultures were pulsed with 0.5 μCi $^3$H-thymidine for the final 6 hours of a 6-day incubation period. Cultures were harvested and counted as above using an automatic cell harvester and standard liquid scintillation counting.

One of the 3-alkoxy-benzo[b]thiophene-2-carboxamides contained here [5-methoxy-3-(1-methylethoxy)-benzo[b]thiophene-2-carboxamide-1-oxide, Example 28] was active in mycobacterium footpad edema (MFE), a subacute model of inflammation. This compound has an $ID_{40}$ of 10.9 mg/kg in MFE. The details of this assay are as follows:

METHOD FOR DETERMINING THE INHIBITION OF MYCOBACTERIUM FOOTPAD EDEMA BY 5-METHOXY-3-(1-METHYLETHOXY) BENZO[b]THIOPHENE-2-CARBOXAMIDE-1-OXIDE

Mycobacterium butyricum (5 mg/mL) was prepared by sonication in paraffin oil for 10 minutes in an ice bath. Footpad edema was induced on Day 0 by injecting 0.1 mL of the Mycobacterium mixture into the left hindpaw of lightly anesthetized rats. Swelling in the injected hindpaw was determined by mercury plethysmography on Days 1, 2, and 3. Groups of rats were treated with test compounds (suspended in 0.5% hydroxypropyl methylcellulose with 0.2% Tween 80 or vehicle 1 hour before Mycobacterium injection and on Days 1 and 2. Inhibition of swelling is determined by comparing the change in hindpaw volume in compound- and vehicle-treated rats.

The inhibition of cyclooxygenase and 5-lipoxygenase by certain of the compounds of the present invention are shown in Table 4. The testing methods used are described as follows:

TABLE 4

Inhibition of 5-Lipoxygenase and Cyclooxygenase by 3-Alkoxy-benzo[b]thiophene-2-carboxamides

| Example Number | R | R-3 | R-5 | ARBL/ARBC IC$_{50}$ ($\mu$M) or % Inhibition at 10 $\mu$M | 5-LO (% Inhibition at 30 $\mu$M) |
|---|---|---|---|---|---|
| 1 | H | iPr | OMe | 36 | 13% |
| 12 | Ph-p-COOH | iPr | OMe | 36/89 | 16% |
| 2 | H | iPr | H | N/N | NA |
| 9 | H | Ph | OMe | N/N | NA |

N = Less than 40% inhibition at 10 $\mu$M
NA = Less than 4% inhibition at 30 $\mu$M Materials The rat basophilic leukemia cell line (RBL-1) was obtained from the American Type Culture Collection (Rockville, Md.).

Radioimmunoassay (RIA) kits of LTB$_4$ and PGF$_{2\alpha}$ were obtained from Amersham (Arlington Heights, IL) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate-buffered saline, pH 7.4 (PBS; NaCl, 7.1 g; Na$_2$HPO$_4$, 1.15 g; KH$_2$PO$_4$, 0.2 g; and KCl, 0.2 g/L). Cells are finally suspended in PBS containing 1.0 mM calcium at a density of 2×10$^6$ cells/mL. Cells are incubated with and without test agent (in DMSO) (1% DMSO is without effect on arachidonic acid metabolism) for 10 minutes at room temperature. Calcium ionophore A23187 (5 $\mu$M) is added and cells are incubated for 7 minutes at 37° C. The reaction is stopped by chilling the tubes on ice for 10 minutes. Cells are separated by centrifugation and the supernatant is stored at −20° C. Aliquots (100 $\mu$L) are analyzed for LTB$_4$ and PGF$_{2\alpha}$ using radioimmunoassay kits as provided by the supplier.

PROTOCOL FOR 5-LIPOXYGENASE INHIBITION ASSAY

Compounds are evaluated for inhibition of 5-lipoxygenase activity contained in the 20,000 xg supernatant from cultured rat basophilic leukemia (RBL) cells. Incubations contained 5% (v/v) RBL 20,000 xg supernatant in assay buffer (10 mM BES, 10 mM PIPES, 1 mM EDTA, 0.75 mM CaCl2, 1 mMATP, 100 mMNaCl, pH 6.8). DMSO vehicle (2% v/v) with and without inhibitors is preincubated with the enzyme for 20 minutes at 37° C. before initiating the 5-lipoxygenase catalyzed reaction by adding 3.3 mmol [$^{14}$C]arachidonic acid (55.8 mCi/mmol, New England Nuclear, Boston, Mass.) dissolved in 5 $\mu$L 0,028% (v/v) aqueous NH$_4$OH. After 20 minutes of additional incubation at 37° C., reactions are terminated by the addition of three volumes of methanol containing 100 $\mu$g triphenylphosphine. Samples are then analyzed by HPLC with radiometric detection for 5-lipoxygenase reaction products.

All treatments are evaluated in duplicate and percent inhibition is computed by comparing the products formed in treatment incubations to the mean product formation in the vehicle control group. The 50% inhibitory concentration (IC$_{50}$) values are computed by regression analysis of the linear portion of percentage inhibition of 5-HETE formation vs log$_{10}$ inhibitor concentration curves.

The compounds of the present invention where R$_2$ is hydrogen are preferably prepared from the corresponding benzo[b]thiophene-2-carboxylic acids. The starting carboxylic acids are prepared as described in U.S. Pat. No. 4,703,503, which is incorporated herein by reference. As depicted in Scheme 1 below, the benzo[b]thiophene-2-carboxylic acid is first treated with a coupling agent, preferably 1,1'-carbonyldiimidazole (CDI), in a solvent such as tetrahydrofuran or acetonitrile to form the corresponding imidazolide or other leaving group. Alternatively, the benzo[b]thiophene-2-carboxylic acid is converted to the acid halide via a reagent such as thionyl chloride, or preferably oxalyl chloride with a catalytic amount of dimethylformamide in a solvent such as methylene chloride or tetrahydrofuran. Subsequent reaction with aqueous ammonium hydroxide or ammonia gas gives the desired primary benzo[b]thiophene-2-carboxamides.

The primary amides can also be prepared by 2-carboxylic acid ester with lithium amide in liquid ammonia in the presence of a co-solvent such as tetrahydrofuran.

Reaction with an oxidizing agent, preferably hydrogen peroxide in acetic acid, converts the benzo[b]thiophene-2-carboxamides to the benzo[b]thiophene-2-carboxamide -1-oxides or benzo[b]thiophene-2-carboxamide -1,1'-dioxides depending on the conditions used. With increased temperature or an excess of oxidizing agent the benzo[b]thiophene-2-carboxamide -1-oxides are further oxidized to the benzo[b]thiophene -2-carboxamide -1,1'- dioxides.

Conditions within the description of Scheme 1 and variations in the description are known or can readily be determined from analogous reactions known to one skilled in the art.

SCHEME 1

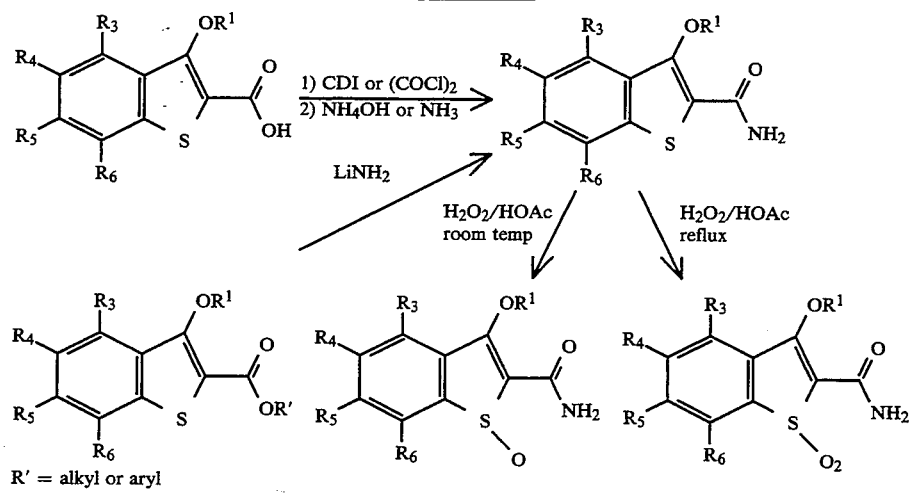

R' = alkyl or aryl

As depicted in Scheme 2, a similar procedure is used to prepare the secondary benzo[b]thiophene-2-carboxamides. Instead of aqueous ammonium hydroxide, the intermediate imidazolide or acid chloride is reacted with a primary amine in the presence or absence of a base such as triethylamine or 1,8-diazabicyclo[5.4.0]-undec-7-ene (DBU). When the amine is in the form of its HCl salt, additional base is required to obtain the free amine.

Once again, by modification of the oxidizing conditions, the 1-oxide or the 1,1'-dioxide analogs can be obtained. Conditions within the description of Scheme 2 and variations in the description are known or can readily be determined from analogous reactions known to one skilled in the art.

SCHEME 3

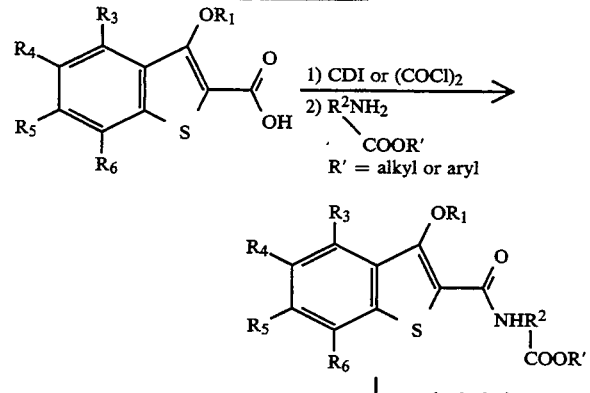

SCHEME 2

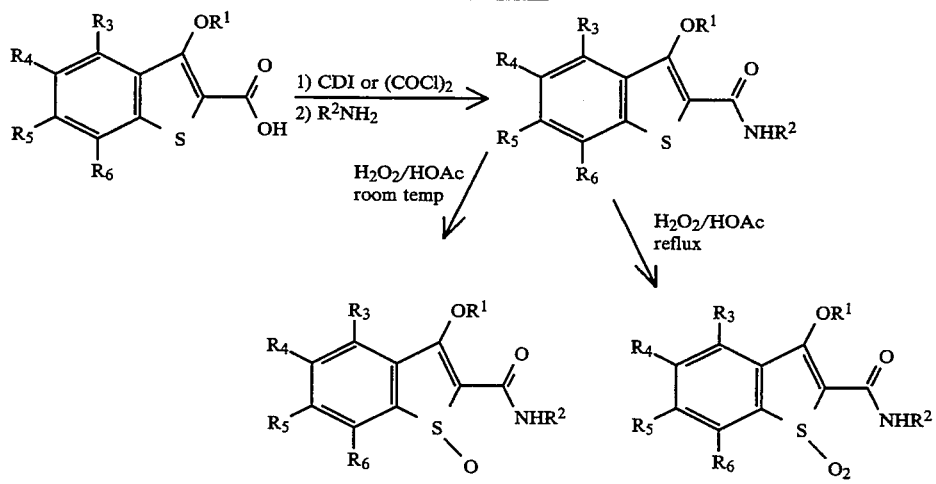

Scheme 3 shows the preparation of secondary benzo[b]thiophene-2-carboxamides containing a carboxylic acid functionality. These compounds are prepared via an intermediate ester. As in Scheme 2, the benzo[b]thiophene-2-carboxylic acid is activated and then treated with an amine that contains the desired ester residue. The amine can be in the form of its HCl salt. The intermediate is isolated and the ester functionality is hydrolyzed, preferably with sodium hydroxide in aqueous ethanol, to give the desired carboxylic acid.

-continued
SCHEME 3

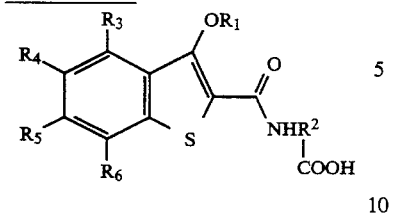

Those compounds where one or more of $R_3$–$R_6$ is hydroxy are prepared via an intermediate that has a suitable hydroxy protecting group. As an example, Scheme 4 shows the preparation of 5-hydroxybenzo[b]-thiophene-2-carboxamides. The amides are prepared from the corresponding acid containing a hydroxy group protected as its benzyl ether. The benzyl group is then removed, preferably by hydrogenation. Other protecting groups, such as silyl groups, can also be used and later removed using standard methodology.

SCHEME 4

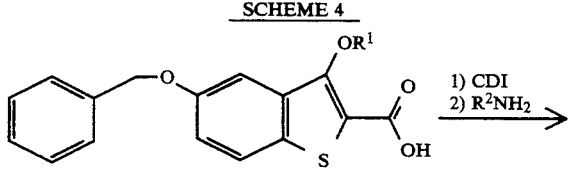

-continued
SCHEME 4

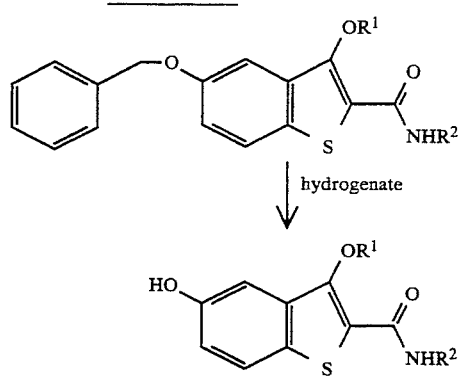

Schemes 5 and 6 present alternate and improved routes for the preparation of benzo[b]thiophene-2-carboxamide-1-oxides and benzo[b]thiophene-2-carboxamide-1,1'-dioxides. The benzo[b]thiophene-2-carboxylic acids can be oxidized to the corresponding 1-oxides with trans-2-phenylsulfonyl3-phenyl oxaziridine, in a solvent such as $CH_2Cl_2$ or acetone, or to the corresponding 1,1-dioxides with hydrogen peroxide in acetic acid. The benzo[b]-thiophene-2-carboxylic acids are converted to the desired amides via initial formation of the sodium salt, then the acid chloride. Addition of ammonia provides the primary 2-carboxamides. Addition of primary amines provides the secondary amides.

The benzo[b]thiophene-2-carboxamides can also be oxidized to the corresponding benzo[b]thiophene2-carboxamide-1-oxides with either trans-2-phenylsulfonyl-3-phenyl oxaziridine or selenium dioxide and hydrogen peroxide in a solvent such as methanol. Use of an excess of selenium dioxide and hydrogen peroxide provides the benzo[b]thiophene-2-carboxamide-1,1'-dioxides.

SCHEME 5

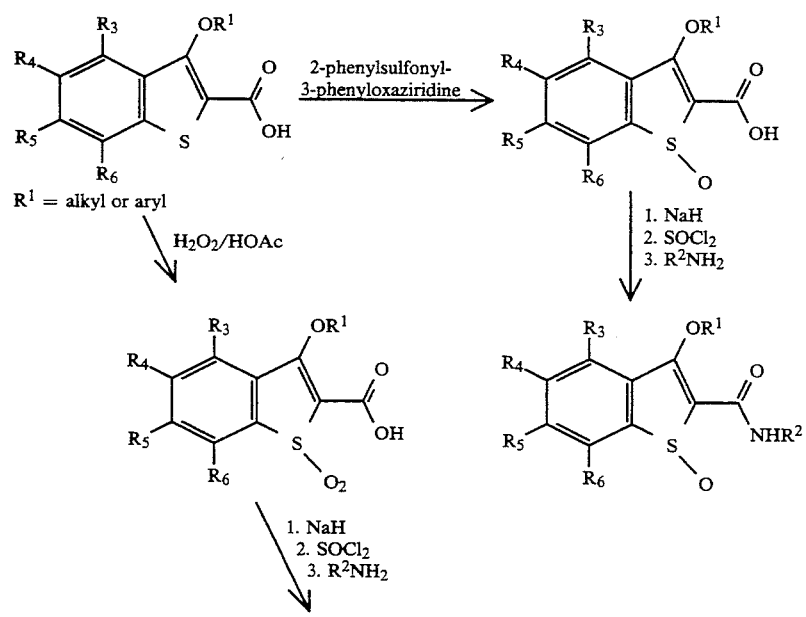

SCHEME 5

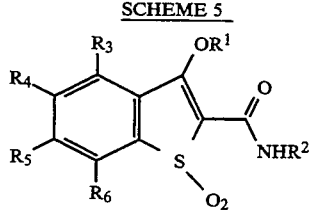

SCHEME 6

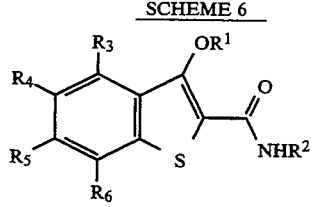

2-phenylsulfonyl-
3-phenyloxaziridine
or
SeO₂/H₂O₂/MeOH

SeO₂/H₂O₂/MeOH

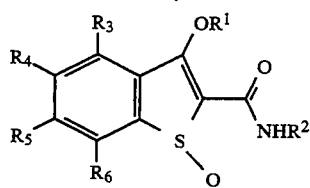

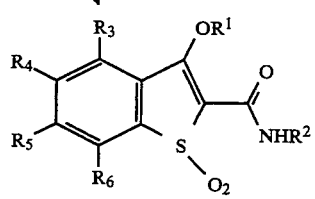

The following examples are illustrative of the preparation of the compounds of the present invention.

EXAMPLE 1

The preparation of 5-methoxy-3-(1-methylethoxy)-benzo[b]thiophene-2-carboxamide is found in U.S. Pat. No. 4,703,053.

EXAMPLE 2

The preparation of 3-(1-methylethoxy)benzo[b]thiophene-2-carboxamide is found in U.S. Pat. No. 4,703,053.

General procedure for the preparation of primary benzo[b]thiophene -2-carboxamides from the corresponding benzo [hi thiophene -2-carboxylic acid.

This procedure was used to prepare Examples 3 to 9 and also 30 to 31. For the preparation of the acids see U.S. Pat. No. 4,703,053.

To 1 mM of a suitably substituted benzo[b]thiophene-2-carboxylic acid in 10 mL of dry tetrahydrofuran is added 1.3 mM of N,N-carbonyldiimidazole. The solution is heated at reflux for 1 hour, then allowed to cool to room temperature. An excess of aqueous ammonium hydroxide (2 mL) is added and the solution is stirred at room temperature for 30 minutes. The mixture is partitioned between ethyl acetate and brine. The organic layer is dried over magnesium sulfate, filtered, and concentrated in vacuo. The crude product is purified by flash chromatography, eluting with 1:1 hexane:ethyl acetate to provide the desired benzo[b]thiophene2-carboxamides as analytically pure materials.

EXAMPLE 3

5-Chloro-3-(1-methylethoxy)benzo[b]thiophene-2-carboxamide (92%); mp 165°–167° C.

EXAMPLE 4

5-Methyl -3-(1-methylethoxy)benzo[b]thiophene-2-carboxamide (94%); mp 153°–154° C.

EXAMPLE 5

3-(1-Methylethoxy)-5-nitrobenzo[b]thiophene2-carboxamide (85%); mp 205°–207° C.

EXAMPLE 6

7-Methoxy-3-(1-methylethoxy)benzo[b]thiophene2-carboxamide (91%); mp 157°–159° C.

EXAMPLE 7

3,5-Dimethoxybenzo[b]thiophene-2-carboxamide (70%); mp 184°–185° C.

EXAMPLE 8

5-Methoxy-3-(phenylmethoxy)benzo[b]thiophene2-carboxamide (72%); mp 149°–151° C.

EXAMPLE 9

Note: Instead of 1,1'-carbonyldiimidazole, the corresponding acid was treated with oxalyl chloride, then with aqueous ammonium hydroxide.

5-Methoxy-3-(phenoxy)benzo[b]thiophene -2-carboxamide (84%); mp 197.5°–198.5° C.

EXAMPLE 10

5-Hydroxy-3-(1-methylethoxy)benzo[b]thiophene-2-carboxamide

A mixture of 3-(1-methylethoxy) -5-phenylmethoxy)-benzo[b]thiophene-2-carboxamide (120 mg, 0.35 mmol) [prepared via the general method given above]and 20%

Pd on carbon (50 mg) in 40 mL of acetic acid is hydrogenated for 72 hours. The catalyst is removed by filtration and the filtrate concentrated in vacuo. The crude product is chromatographed, eluting with a gradient of 1:1 to 1:2 hexane:ethyl acetate, providing 49.4 mg of 5-hydroxy-3-(1-methylethoxy)benzo[b]thiophene-2-carboxamide (56%); mp 237°–240° C. (dec) .

EXAMPLE 11

6-Methoxy-3-(1-methylethoxy)benzo[b]thiophene-2-carboxamide

Excess lithium (74 mg, 10 mM) is added portionwise to a −78° C. solution of a catalytic amount of ferric nitrate in 10 mL of liquid ammonia. The dry ice/acetone bath is removed to allow the reaction to warm to reflux. When the gray color of lithium amide remains for 10 minutes, 2 mL of freshly distilled tetrahydrofuran is added slowly followed by a solution of methyl 6-methoxy-3-(-methylethoxy)benzo[b]thiophene-2-carboxylic acid (200 mg, 0.71 mM) in 2 mL of tetrahydrofuran. The ammonia is allowed to evaporate. The reaction solution is diluted with ethyl acetate, washed with aqueous hydrochloric acid, followed by water, then brine. The organic phase is dried over magnesium sulfate, filtered, and concentrated in vacuo. The crystalline residue is suspended in 1:9 ethyl acetate:hexane, filtered, and dried at 50° C. in vacuo affording 125 mg (66%) of colorless crystals, mp 164°–166° C.

EXAMPLE 12

4-[[[5-Methoxy-3-(1-methylethoxy)benzo[b]thien-2-yl]carbonyl]amino]benzoic acid

To 5-methoxy-3-(1-methylethoxy)benzo[b]thiophene-2-carboxylic acid (353 rag, 1.32 mmol) in 5 mL of dry tetrahydrofuran is added oxalyl chloride (140 μL, 1.60 mmol) followed by one drop of dimethylforrnarnide. The solution is stirred at room temperature for 1 hour, then concentrated in vacuo. The resulting solid is added portionwise to a 0° C. solution of methyl 4-aminobenzoate (250 mg, 1.65 mmol) and triethylamine (220 μL, 1.58 mmol) in 10 mL of tetrahydrofuran. The mixture is stirred at room temperature for 1 hour, then partitioned between ethyl acetate and brine. The organic layer is dried over magnesium sulfate, filtered, and concentrated in vacuo. The crude product is purified by flash chromatography, eluting with 3:1 hexane:ethyl acetate to provide 284 mg of product, mp 138°–142° C.

A mixture of 4.0 g of methyl 4-[[[5-methoxy-3-(1-methylethoxy)benzo[b]thien-2-yl]carbonyl]amino]benzoate and 2 g of 50% NaOH in 100 mL of 10% aqueous methanol is heated on a steam bath for 15 minutes, then poured onto ice and acidified with 10% HCl. The resulting gum is extracted into 500 mL of diethyl ether. The organic phase is dried over magnesium sulfate, filtered, and concentrated in vacuo. The crude solid is triturated with t-butyl methyl ether to provide 2.5 g of product; mp 236°–239° C. (dec).

EXAMPLE 13

3-[[[5-Methoxy-3-(1-methylethoxy)benzo[b]thien-2-yl]carbonyl]amino]benzoic acid

Following a procedure analogous to Example 12, 5-methoxy-3-(1-methylethoxy)benzo[b]thiophene-2-carboxylic acid (7.0 g, 26 mmol) and ethyl 3-aminobenzoate (4.3 g, 26 mmol) provides 8.5 g (78%) of the intermediate ester. Saponification of the crude ester followed by recrystallization from aqueous ethanol gives 4.2 g (53%) of product; mp 197°–200° C. (dec).

EXAMPLE 14

Ethyl 2-[[[5-methoxy-3-(1-methylethoxy)benzo[b]thien-2-yl]carbonyl]amino]benzeneacetate Following a procedure analogous to Example 12, 5-methoxy-3-(1-methylethoxy)benzo[b]thiophene-2-carboxylic acid (1.04 g, 3.9 mmol) and ethyl 2-aminobenzoate (. 67 g, 4.1 mmol) provides 0.81 g (51%) of product; mp 105°–106 ° C.

EXAMPLE 15

2-[[[5-Methoxy-3-(1-methylethoxy)benzo[b]thien2-yl]carbonyl]amino]benzoic acid

Saponification of 0.25 g of ethyl 2-[[[5-methoxy-3-(1-methylethoxy)benzo[b]thien-2-yl]carbonyl]arnino]benzeneacetate gives 0.17 g (72%) of product; mp 239°–242° C. (dec) .

EXAMPLE 16

4-[[[5-Methoxy-3-(1-methylethoxy)benzo[b]thien-2-yl]carbonyl]aminomethyl]benzoic acid A solution of 5-methoxy-3-(1-methylethoxy)benzo[b]thiophene-2-carboxylic acid (500 mg, 2.0 mmol) and 1,1'-carbonyldiimidazole (421 mg, 2.6 mmol) in 20 mL of tetrahydrofuran is heated at reflux for 1 hour. After cooling to 0° C., the HCl salt of methyl 4-(aminomethyl)benzoate (524 mg, 2.6 mmol) is added followed by triethylamine (362 μL, 2.6 mmol). The mixture is stirred at room temperature for 4 hours. The mixture is partitioned between ethyl acetate and 1N HCl. The organic layer is washed with water, then brine. The organic layer is next dried over magnesium sulfate, filtered, and concentrated in vacuo. The crude product is purified by flash chromatography, eluting with a gradient of 1:9 to 15:85 ethyl acetate:methylene chloride to provide 49 mg of the desired intermediate ester. The ester and 15 mg of LiOH-H$_2$O in 2 rnL of 50% aqueous methanol are heated at reflux for 1 hour. The organic layer is washed with water, then brine, dried over magnesium sulfate, filtered, and concentrated in vacuo. Recrystallization from ethyl acetate:hexane gives 32.1 mg of product (65% from the ester); mp 142°–143° C. (dec).

EXAMPLE 17

Methyl 4-E [[5-Methoxy-3-(1-methylethoxy)benzo[b]thien-2-yl]carbonyl]amino]benzeneacetate To 5-methoxy-3-(1-methylethoxy)benzo[b]thiophene-2-carboxylic acid (500 mg, 2.0 mmol) in 20 mL of dry tetrahydrofuran is added oxalyl chloride (262 μL, 3.0 mmol) followed by one drop of dimethylformamide. The HCl salt of methyl 4-aminophenylacetate (605 mg, 3.0 mmol) is added, followed by triethylarnine (1.4 mL, 0 mmol). The mixture is stirred at room temperature overnight. The mixture is partitioned between ethyl acetate and 1N HCl. The organic layer is washed with water, then brine. The organic layer is next dried over magnesium sulfate, filtered, and concentrated in vacuo. The crude product is purified by flash chromatography, eluting with a gradient of 1:1 ethyl acetate:hexane to only ethyl acetate to provide 692 mg (84%) of product; mp 111°–113° C.

EXAMPLE 18

4-[[[5-Methoxy-3-(1-methylethoxy)benzo[b]thien2-yl]carbonyl]amino]benzeneacetic acid Methyl 4-[[[5-methoxy-3-(1-methylethoxy)benzo[b]-thien-2-ylcarbonyl]amino]phenylacetate (300 mg, 0.73 mmol) and 91 mg of LiOH-H20 in a mixture of 5 mL of methanol and 2 mL of water are heated at reflux for 2 hours. The reaction mixture is partitioned between ethyl acetate and aqueous HCl. The organic layer is washed with water, then brine, dried over magnesium sulfate, filtered, and concentrated in vacuo. Recrystallization from ethyl acetate:hexane gives 247 mg (85%) of product; mp 195.5°–196.5° C.

EXAMPLE 19

Methyl 3-[[[5-Methoxy-3-(1-methylethoxy)benzo[b]thien-2-yl]carbonyl]amino]benzeneacetate Following a procedure analogous to that of Example 17; 5-methoxy-3-(1-methylethoxy)benzo[b]thiophene-2-carboxylic acid (500 mg, 2.0 mmol) and the HCl salt of methyl 3-aminophenylacetate (605 mg, 3.0 mmol) provide 506 mg (61%) of product; mp 103°–106° C.

EXAMPLE 20

3-[[[5-Methoxy-3-(1-methylethoxy)benzo[b]thien-2-yl]carbonyl]amino]benzeneacetic acid Following a procedure analogous to that of Example 18; methyl 3-[[[5-methoxy-3-(1-methylethoxy)benzo[b]-thien-2-yl]carbonyl]amino]phenylacetate (250 mg, 0.60 mmol) and 76 mg of LiOH—H$_2$O provide 172 mg (72%) of product; mp 155°–156° C.

EXAMPLE 21

Methyl 5-[[[5-methoxy-3-(1-methylethoxy)benzo[b]thien2-yl]carbonyl]amino]pentanoate A solution of 5-methoxy-3-(1-methylethoxy)benzo[b]thiophene-2-carboxylic acid (500 mg, 2.00 mmol) and 1,1'-carbonyldiimidazole (421 mg, 2.60 mmol) in 20 mL of tetrahydrofuran is heated at reflux for 1 hour. After cooling to 0° C., the HCl salt of methyl 5-aminovalerate (787 mg, 4.7 mmol) is added followed by triethylamine (836 µL, 6.0 mmol). The mixture is heated at reflux overnight. The mixture is partitioned between ethyl acetate and 1N HCl. The organic layer is washed with in HCl, saturated NaHCO$_3$, then brine. The organic layer is next dried over magnesium sulfate, filtered, and concentrated in vacuo. The crude product is purified by flash chromatography, eluting with 1:9 ethyl acetate:hexane to provide 530 mg (70%) of product; mp 82°–84° C.

EXAMPLE 22

5-[[[5-Methoxy-3-(1-methylethoxy)benzo[b]thien2-yl]carbonyl]amino]pentanoic acid Methyl 5-[[5-methoxy-3-(1-methylethoxy)benzo[b]-thien-2-yl]carbonyl]aminovalerate (250 mg, 0.66 mmol) and 83 mg of LiOH-H$_2$O in a mixture of 5 mL of methanol and 2 mL of water are stirred at room temperature for 7 hours. The reaction mixture is partitioned between ethyl acetate and aqueous HCl. The organic layer is washed with water, then brine, dried over magnesium sulfate, filtered, and concentrated in vacuo. Recrystallization from ethyl acetate:hexane gives 205 mg of product (85%); mp 135°–137° C.

EXAMPLE 23

3-[[[5-Methoxy-3-(1-methylethoxy)benzo[b]thien2-yl]carbonyl]amino -2-thiophenecarboxylic acid To 5-methoxy-3-(1-methylethoxy)benzo[b]thiophene-2-carboxylic acid (7.0 g, 26 mmol) in 100 mL of dry tetrahydrofuran is added oxalyl chloride (2.8 mL, 32 mmol) followed by four drops of dimethylformamide. The solution is stirred at room temperature for 45 minutes, then concentrated in vacuo. The resulting solid is dissolved in dry tetrahydrofuran and added dropwise to a solution of methyl 3-amino-2-thiophenecarboxylate (4.5 g, 29 mmol) and triethylamine (11 mL, 79 mmol) in 75 ml of tetrahydrofuran. The mixture is stirred at room temperature for 2 hours, then quenched with 10% HCl. The mixture is extracted with ethyl acetate, and the combined organic layers washed with 5% sodium bicarbonate and brine. The organic layer is dried over magnesium sulfate, filtered, and concentrated in vacuo. The crude product is recrystallized from t-butylmethyl ether to provide 4.5 g of a white solid; mp 131°–137° C.

4.4 g (11 mmol) of this ester is combined with 50% aqueous sodium hydroxide (4.0 g, 50 mmol) in 10% aqueous methanol (200 mL) and 40 mL of tetrahydrofuran. The mixture is heated on the steam bath for hours, cooled, and added to 60 g of ice. After acidification with 10% HCl, the precipitated solid is filtered and washed with water. Recrystallization from 95% ethanol gives 3.0 g (71%) of product; mp 223°–227° C. (dec).

General procedure for the preparation of secondary benzo[b]thiophene-2-carboxamides from the corresponding acid:

A solution of 1 mM of a suitably substituted benzothiophene-2-carboxylic acid and 1.3 mM of 1,1'-carbonyldiimidazole in dry tetrahydrofuran is refluxed for 1 to 2 hours. The reaction solution is cooled to 0° C. and an excess amount of a primary amine is added. The reaction is diluted with ethyl acetate and washed with aqueous hydrochloric acid, followed by water, then brine. The organic phase is dried over magnesium sulfate, filtered, and concentrated in vacuo. Analytical products are obtained via column chromatography and/or recrystallization.

EXAMPLE 24

5-Methoxy-N-methyl-(3-(1-methylethoxy)benzo[b]thiophene-2-carboxamide (55%); mp 104°–105° C.

EXAMPLE 25

N-Ethyl-(5-methoxy-3-(1-methylethoxy)benzo[b]thiophene-2-carboxaraide (62%); mp 60°–62° C.

EXAMPLE 26

5-Methoxy-3-(1-methylethoxy)-N-phenylbenzo[b]thiophene-2-carboxaraide (27%); mp 116°–118° C.

EXAMPLE 27

5-Methoxy-3-(1-methylethoxy)-N-(phenylmethyl)benzo[b]thiophene-2-carboxamide (81%); mp 85°–86° C.

EXAMPLE 28

5-Methoxy-3-(1-methylethoxy)benzo[b]thiophene-2-carboxamide-1-oxide

Preparation A

A solution of 5-methoxy-3-(1-methylethoxy)benzothiophene-2-carboxaraide (250 mg, 0.94 mM) and 30% hydrogen peroxide (4 mL, 40 mM) in acetic acid (9.5 mL) is stirred at room temperature for 8 hours. The reaction solution is diluted with water and the pH is adjusted to 7 with aqueous sodium hydroxide and saturated sodium bicarbonate. The organic materials are extracted with ethyl acetate. The organic phase is washed with a saturated solution of sodium bicarbonate, followed by water, then brine, and dried over magnesium sulfate, filtered, and concentrated in vacuo. The residue is crystallized twice from ethyl acetate:hexane to give 60 mg (23%) of the 1-oxide; mp 163°–164° C.

Preparation B

A solution of 5-methoxy-3-(1-methylethoxy)benzothiophene-2-carboxylic acid (30 g, 112 mmol) and (±)-trans-2-(phenylsulfonyl)-3-phenyloxaziridine (35 g, 135 mmol) [prepared according to Org. Syn., 1987;66:203]in chloroform (500 mL) is stirred at room temperature for 20 hours. The reaction mixture is filtered. The solid is washed with two portions of 1:1 chloroform:hexane. The filtrate is stirred at room temperature for 8 hours. Additional (±)-trans2-(phenylsulfonyl)-3-phenyloxaziridine (17 g, 66 mmol) is added and stirring is continued overnight. The resulting solid is collected by filtration and the filtrate is stirred at room temperature overnight. The precipitated solids are removed by filtration. The collected solids are combined and recrystallized from EtOAc/MeOH to provide 16.6 g (53%) of analytically pure 5-methoxy-3-(1-methylethoxy)benzo[b]thiophene-2-carboxylic acid-1-oxide; mp 184°–187° C. Further recrystallization provides additional crops [4.3 g (14%) and 2.1 (7%)].

Sodium hydride (326 mg, 8.15 mmol) is washed free of oil and added to a room temperature solution of 5-methoxy-3-(1-methylethoxy)benzo[b]thiophene-2-carboxylic acid-1-oxide (2.30 g, 8.1 mmol) in a solvent system consisting of 25 mL of DMF and 75 mL of THF. After stirring at room temperature for 1.5 hours, the thick precipitate is cooled to -10° C. and thionyl chloride (713 μL, 9.78 mmol) is added. After 2 hours the solution is cooled to −78° C. resulting in the formation of a suspension. Ammonia gas is introduced under the surface for about 1 minute. After 10 minutes the reaction mixture is poured into a mixture of 6N HCl and brine. The organic phase is washed with additional acidic brine followed by saturated NaHCO3, then brine. The organic layer is dried over MgSO4, filtered, and concentrated in vacuo. The resulting solid is recrystallized from EtOAc:hexane to provide 1.44 g (63%) of 5-methoxy-3-(1-methylethoxy)benzo[b]thiophene-2-carboxamide-1-oxide; mp 168.5°–169.5° C.

EXAMPLE 29

5-Methoxy-3-(1-methylethoxy)benzo[b]thiophene2-carboxamide 1,1'-dioxide

A solution of 5-methoxy-3-(1-methylethoxy)benzothiophene-2-carboxamide (250 mg, 0.94 mM) and 30% hydrogen peroxide (4 mL, 40 mM) in acetic acid (9.5 mL) is heated at reflux for 6 hours. The reaction solution is diluted with ethyl acetate and washed five times with brine, dried over magnesium sulfate, filtered, and concentrated in vacuo. The residue is crystallized from ethyl acetate:hexane to give 67 mg (24%) of the dioxide; mp 151°–153° C.

EXAMPLE 30

3-(1,1-Dimethylethoxy)-5-methoxybenzo[b]thiophene2-carboxamide

Prepared by a procedure analogous to Example 2 (74%); mp 180°–181° C.

EXAMPLE 31

6-Chloro-3-(1-thylethoxy)benzo[b]thiophene-2-carboxamide

Prepared by a procedure analogous to Example 2 (90%); mp 176°–178° C.

EXAMPLE 32

5-Amino-3-(1-methylethoxy)benzo[b]thiophene-2-carboxamide

A mixture of 3-(1-methylethoxy) -5-nitrobenzo[b]-thiophene-2-carboxamide (104 mg, 0.37 mmol) and 5% Pd on carbon (10 mg) in 20 mL of acetic acid is hydrogenated for 1.5 hours. The catalyst is removed by filtration and the filtrate concentrated in vacuo. The crude product is chromatograhed, eluting with 1:2 hexane:ethyl acetate, providing 62 mg of 5-amino-3-(1-methylethoxy)benzo[b]thiophene-2-carboxamide (67%); mp 150°–151° C.

EXAMPLE 33

Methyl 4-[[[5-methoxy-3-(1-methylethoxy)benzo[b]thien-2-yl]carbonyl]amino]butanoate Prepared by a procedure analogous to Example 21 (93%); mp 35°–36 . 5° C.

EXAMPLE 34

4-[[[5-Methoxy-3-(1-methylethoxy)benzo[b]thien-2-yl]carbonyl]amino]butanoic acid Prepared by a procedure analogous to Example 22 (77%); mp 101°–102° C (dec).

EXAMPLE 35

5-Methoxy-3-(1-methylethoxy)-N-(1-methylethyl)benzo[b]thiophene-2-carboxamide

Prepared by a procedure analogous to Example 24, (76%); mp 64.5°–65.5° C.

EXAMPLE 36

Ethyl 6-[[[5-methoxy-3-(1-methylethoxy)benzo[b]thien-2-yl]carbonyl]amino]-3-pyridinecarboxylate Following a procedure analogous to Example 12, 5-methoxy-3-(1-methyl ethoxy)benzo[b]thiophene-2-carboxylic acid (1.07 g, 4 mmol ) and ethyl 6-aminonicotinate (690 mg, 4.2 mmol) provides 90 mg (6%) of product; mp 131°–133° C.

EXAMPLE 37

6-[[[5-Methoxy-3-(1-methylethoxy)benzo[b]thien-2-yl]carbonyl]amino-3-pyridinecarboxylic acid Saponification of 345 mg of ethyl 6-[[[5-methoxy-3-(1-methylethoxy)benzo[b]thien -2-yl]carbonyl]amino]-3-pyridinecarboxylate gives 94 mg (29%) of product; mp 242°–247° C. dec.

EXAMPLE 38

Ethyl 2-[[[5-methoxy-3-(1-methylethoxy)benzo[b]thien-2-yl]carbonyl]amino]-4-thiazoleacetate Following a procedure analogous to Example 2, 5-methoxy-3-(1-methylethoxy)benzo[b]thiophene-2-carboxylic acid (1.033 g, 3.88 mmol) and ethyl-2-amino-4-thiazoleacetate (709 mg, 4.37 mmol) gives 1.22 g (73%) of product; mp 91°–92° C.

EXAMPLE 39

2-[[[5-Methoxy-3-(1-methylethoxy)benzo[b]thien-2-yl]carbonyl]amino]-4-thiazoleacetic acid Saponification of 521 mg of ethyl 2-[[[5-methoxy-3-(1-methylethoxy)benzo[b]thien-2-yl]carbonyl]amino]-4-thiazoleacetate gives 135 mg (28% of product; mp 189°–191° C.

EXAMPLE 40

3-Methoxy-4-[[[5-methoxy-3-(1-methylethoxy)benzo[b]thien-2-yl]carbonyl]amino]benzoic acid Following a procedure analogous to Example 12, 5-methoxy-3-(1-methylethoxy)benzo[b]thiophene-2-carboxylic acid (230 mg, 0.86 mmol) and methyl 4-amino-3-methoxybenzoate (310 mg, 1.38 mM) [obtained by esterification of 4-amino-3-methoxybenzoic acid (Aldrich) with MeOH/AcCl]provides 269 mg (73%) of product; mp 278° C. dec. Saponification of 100 mg of methyl 3-methoxy-4-[[[5-methoxy-3-(1-methylethoxy)benzo [b]thien-2-yl]carbonyl]amino]benzoate gives 48 mg (50%) of product; mp 278°–281° C. dec.

EXAMPLE 41

Methyl 2-hydroxy-4-[[[5-methoxy-3-(1-methylethoxy)benzo[b]-thien-2-yl]carbonyl]amino]benzoate Following a procedure analogous to Example 12, 5-methoxy-3-(1-methylethoxy)benzo[b]thiophene-2-carboxylic acid (200 mg, 0.75 mmol) and methyl 4-aminosalicylate (117 mg, 0.70 mmol) [obtained by esterification of 4-aminosalicylic acid, sodium salt (Sigma) with iodomethane] provides 172 mg (59%) of product; mp 158.5°–160° C.

EXAMPLE 42

2-Hydroxy-4-[[[5-methoxy-3-(1-methylethoxy)benzo[b]thien-2-yl]carbonyl]arnino]benzoic acid Saponification of 100 mg of methyl 2-hydroxy-4-[[[5-methoxy-3-(1-methylethoxy)benzo[b]thien-2-yl]carbonyl]amino]benzoate gives 74 mg (76%) of product; mp 237°–238° C.

EXAMPLE 43

Methyl 4-[[[5-methoxy-3-(1-methylethoxy)benzo[b]thien-2-yl]carbonyl]amino]benzenesulfonate Following a procedure analogous to Example 12, 5-methoxy-3-(1-methylethoxy)benzo[b]thiophene-2-carboxylic acid (300 mg, 1.1 mmol) and 402 mg, 1.8 mmol) methyl 4-aminobenzenesulfonate [obtained by catalytic hydrogenation of methyl 4-nitrobenzenesulfonate (Aldrich) followed by salt formation] provides 295 mg (56%) of product; mp 176.5°–177° C.

EXAMPLE 44

N-[1-(hydroxymethyl)-1-methylethyl]-5-methoxy-3-(1-methylethoxy)benzo[b]thiophene-2-carboxamide Following a procedure analogous to Example 12, 5-methoxy-3-(1-methylethoxy)benzo[b]thiophene-2-carboxylic acid (2.50 g, 9.4 mmol) and 2-amino-2-methylpropanol (3.7 mL, 38.6 mmol) provides 3.2 g (100%) of product. An analytical sample was obtained by recrystallization from EtOAc/hexane; mp 138°–138.5° C.

EXAMPLE 45

N-Ethyl-5-methoxy-3-(1-methylethoxy)benzo[b]thiophene-2-carboxamide-1-oxide

Selenium dioxide is added to a room temperature solution of N-ethyl-5-methoxy-3-(1-methylethoxy)benzo[b]thiophene-2-carboxamide (195 mg, 0.66 mmol) in 8 mL of MeOH containing 530 µL of hydrogen peroxide (30% aqueous). The reaction mixture is stirred overnight at room temperature. The reaction mixture is poured into EtOAc and saturated NaHCO$_3$. The organic phase is washed with saturated NaHCO$_3$, 1N HCl, then brine. The organic layer is dried over MgSO$_4$, filtered, and concentrated in vacuo. The resulting solid is chromatographed, eluting with a gradient of 1:9 EtOAc:CH$_2$Cl$_2$ to 1:1 EtOAc:CH$_2$Cl$_2$, to provide 96 mg (47%) of N-ethyl-5-methoxy-3-(1-methylethoxy)benzo[b]thiophene-2-carboxamide -1-oxide; mp 88°–90° C.

EXAMPLE 46

5-Methoxy-N-methyl -3-(1-methylethoxy)benzo[b]thiophene-2-carboxamide -1-oxide

Following a procedure analogous to Example 45, 200 mg of 5-methoxy-N-methyl -3-(1-methylethoxy)benzob]thiophene-2-carboxamide is oxidized to provide 65 mg (30%) of product; mp 123°–124° C.

EXAMPLE 47

5-Methoxy-3-(1-methylethoxy)-N-(phenylmethyl)benzo[b]thiophene-2-carboxamide -1-oxide Following a procedure analogous to Example 28, Preparation B, 200 mg (0.71 mmol) of 5-methoxy-3-(1-methylethoxy)benzo[b]thiophene-2-carboxylic acid-1-oxide and 388 µL (3.55 mmol) of benzylamine gives 7 mg (52%) of 5-methoxy-3-(1-methylethoxy)-N-(phenylmethyl)benzo[b]thiophene-2-carboxamide-1-oxide as a yellow gum.

EXAMPLE 48

Methyl 3-[[[5-methoxy-3-(1-methylethoxy)benzo[b]thien-2-yl]carbonyl]amino]benzeneacetate-1-oxide Following a procedure analogous to Example 28, Preparation B, 700 mg (2.48 mmol) of 5-methoxy-3-(1-methylethoxy)benzo[b]thiophene-2-carboxylic acid-1-oxide and 1.90 g (12.4 mmol) of methyl 4-aminobenzoate gives 530 mg (51%) of methyl 3-[[[5-methoxy-3-(1-methylethoxy)benzo[b]thien-2-yl]carbonyl]amino]benzeneacetate-1-oxide; mp 162°–162.5° C. dec.

EXAMPLE 49

5-Hydroxy-3-(1-methylethoxy)benzo[b]thiophene-2-carboxaraide-1-oxide (±)-trans-2-(Phenylsulfonyl)-3-phenyloxaziridine (400 mg, 1.5 mmol) is added to a solution of 5-hydroxy-3-(1-methylethoxy)benzo[b]thiophene-2-carboxamide (300 mg, 1.2 mmol) in 15 mL of acetone. After stirring at room temperature for 48 hours, the reaction mixture is filtered and the precipitate washed with cold acetone to give 200 mg (62%) of 5-hydroxy-3-(1-methylethoxy)-benzo[b]thiophene-2-carboxaraide-1-oxide; mp 190° C. dec.

EXAMPLE 50

5-Methyl-3-(1-methylethoxy)benzo[b]thiophene-2-carboxaraide-1-oxide

Following a procedure analogous to Example 28, Preparation B, 235 mg of 5-methyl-3-(1-methylethoxy)-benzo[b]thiophene-2-carboxylic acid gives 131 mg (53%) of 5-methyl-3-(1-methylethoxy)benzo[b]thiophene-2-carboxylic acid-1-oxide; mp 184°–187° C. 5-Methyl-3-(1-methylethoxy)benzo[b]thiophene-2-carboxylic acid-1-oxide (120 mg) provides 63 mg (52%) of product; mp 175°–177° C.

EXAMPLE 51

5-Methoxy-3-phenoxybenzo[b]thiophene-2-carboxamide-1-oxide

Following a procedure analogous to Example 28, Preparation B, 500 mg of 5-methoxy-3-phenoxy-benzo[b]thiophene-2-carboxylic acid gives 108 mg (21%) of 5-methoxy-3-phenoxybenzo[b]thiophene-2-carboxylic acid-1-oxide; mp 204°–206° C. 5-Methoxy-3-phenoxybenzo[b]thiophene-2-carboxylic acid-1-oxide (200 mg) provides 116 mg (58%) of product; mp 191°–193° C. dec.

EXAMPLE 52

5-Methoxy-3-(1-methylethoxy)-N-(1-methylethoxy)-benzo[b]thiophene-2-carboxamide-1-oxide Following a procedure analogous to Example 45, 200 mg of 5-methoxy-3-(1-methylethoxy)-N-(1-methylethoxy)benzo[b]thiophene-2-carboxamide is oxidized to provide 111 mg (53%) of product as a colorless oil.

EXAMPLE 53

3,5-Dimethoxybenzo[b]thiophene-2-carboxamide-1-oxide

Following a procedure analogous to Example 49, 500 mg of 3,5-dimethoxybenzo[b]thiophene-2-carboxamide is oxidized to provide 100 mg (19%) of product; mp 195° C. dec.

We claim:

1. A compound of the formula

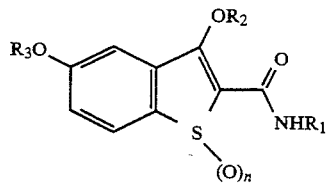

wherein n is the number 0 or 1;
$R_1$ is hydrogen or lower alkyl provided $R_1$ is not hydrogen when n is 0;
$R_2$ is lower alkyl, and
$R_3$ is hydrogen or lower alkyl or a pharmaceutically acceptable salt thereof.

2. A compound of claim 1 wherein n is 0.
3. The compound of claim 1 wherein n is 1.
4. The compound of claim 1 wherein $R_1$ is hydrogen.
5. The compound of claim 1 wherein $R_1$ is lower alkyl.
6. The compound of claim 1 wherein $R_2$ is isopropyl.
7. The compound of claim 1 wherein $R_3$ is hydrogen.
8. The compound of claim 1 wherein $R_3$ is lower alkyl.
9. The compound of claim 1 wherein n is 0, $R_1$ is methyl, $R_2$ is isopropyl and $R_3$ is methyl.
10. The compound of claim 1 wherein n is 1, $R_1$ is hydrogen, $R_2$ is isopropyl and $R_3$ is methyl.
11. The compound of claim 1 wherein n is 1, $R_1$ is methyl, $R_2$ is isopropyl and $R_3$ is methyl.

* * * * *